United States Patent [19]

D'Amore et al.

[11] Patent Number: 4,886,870
[45] Date of Patent: Dec. 12, 1989

[54] BIOERODIBLE ARTICLES USEFUL AS IMPLANTS AND PROSTHESES HAVING PREDICTABLE DEGRADATION RATES

[75] Inventors: Patricia D'Amore, Brookline; Kam W. Leong, Cambridge; Robert S. Langer, Somerville, all of Mass.

[73] Assignee: Massachusetts Institute of Technology, Cambridge, Mass.

[21] Appl. No.: 702,168

[22] Filed: Feb. 15, 1985

Related U.S. Application Data

[63] Continuation-in-part of Ser. No. 613,001, May 21, 1984, which is a continuation of Ser. No. 477,710, Mar. 22, 1983, abandoned.

[51] Int. Cl.$^4$ .................. C08G 63/18; C08G 63/60; C08G 69/44
[52] U.S. Cl. .................. 528/206; 528/271; 524/17; 524/21; 524/599; 424/19; 424/78; 623/1
[58] Field of Search .................. 528/271, 206; 623/1; 524/17, 21, 599; 424/19, 78

[56] References Cited

U.S. PATENT DOCUMENTS

| | | | |
|---|---|---|---|
| 2,071,250 | 2/1937 | Carothers | 160/106 |
| 2,071,251 | 2/1937 | Carothers | 18/54 |
| 2,073,799 | 3/1937 | Hill | 260/112 |
| 2,668,162 | 2/1954 | Lowe | 260/78.3 |
| 2,676,945 | 4/1954 | Higgins | 260/45.7 |
| 2,958,678 | 11/1960 | Conix | 260/78.4 |
| 2,960,493 | 11/1960 | Conix | 260/47 |
| 3,526,612 | 9/1970 | Allphin | 260/78.4 |
| 3,625,214 | 12/1971 | Higuchi | 128/260 |
| 3,766,145 | 10/1973 | Thompson | 260/75 EP |
| 3,811,444 | 5/1974 | Heller et al. | 128/260 |
| 3,914,401 | 10/1975 | Sharabash | 424/19 |
| 3,960,150 | 6/1976 | Hussain et al. | 128/260 |
| 3,976,071 | 8/1976 | Sadek | 128/260 |
| 3,981,303 | 9/1976 | Higuchi et al. | 128/260 |
| 3,986,510 | 10/1976 | Higuchi et al. | 128/260 |
| 3,993,071 | 11/1976 | Higuchi et al. | 128/260 |
| 4,014,987 | 3/1977 | Heller et al. | 424/15 |
| 4,036,227 | 7/1977 | Zaffaroni et al. | 128/260 |
| 4,096,238 | 6/1978 | Zaffaroni et al. | 424/15 |
| 4,489,056 | 12/1984 | Himmelstein et al. | 424/22 |

FOREIGN PATENT DOCUMENTS

| | | |
|---|---|---|
| 6846854 | 4/1964 | Canada . |
| 2590262 | 5/1987 | France . |
| 60-141725 | 7/1985 | Japan . |
| 0840846 | 7/1960 | United Kingdom ............ 528/271 |
| 0840847 | 7/1960 | United Kingdom ............ 528/271 |
| 968715 | 9/1964 | United Kingdom . |

OTHER PUBLICATIONS

Synthesis and Characterization of Bioerodible Polymer For Controlled Drug Release: by Howard Rosen (1980).

Encylopedia of Polymer Science and Technology, vol. 10 Wiley, NYC., 630–653 (1969).

Bucher, John E. and Slade, W. Clifton, The Anhydrides of Isophthalic and Terephthalic Acids, J. Amer. Chem. Soc. 32, 1319 (1909).

Yoda, Naoya, Synthesis of Polyanhydrides, XI., *Makromol. Chem.* 56, 36 (1962).

Yoda, Naoya, Synthesis of Polyanhydrides. XII. Crystalline and High Melting Polyamidepolyanhydride of Methylenebis (p-carboxyphenyl)amide, *Journal of Polymer Science:* Part A, vol. 1, 1323 (1962).

(List continued on next page.)

*Primary Examiner*—John Kight
*Assistant Examiner*—M. L. Moore
*Attorney, Agent, or Firm*—Kilpatrick & Cody

[57] ABSTRACT

A novel series of articles useful as implants and prostheses and methods for their preparation and use are provided which utilize polyanhydride polymeric matrices as a general class of materials. These articles are biocompatible, non-inflammatory and degrade predictably into non-toxic residues after introduction in-vivo. The articles may be formed in any desired dimensions and configuration and may take specific shape as vascular or skin grafts, as biodegradable sutures or as orthopedic appliances such as bone plates and the like.

7 Claims, 6 Drawing Sheets

OTHER PUBLICATIONS

Yoda, Naoya, Synthesis of Polyanhydrides. II. New Aromatic Polyanhydrides with High Melting Points and Fiber-Forming Properties, *Makromol. Chem.* 32, 1 (1959).

Yoda, Naoya, Synthesis of Polyanhydrides X. Mixed Anhydrides of Aromatic and Five-Membered Heterocyclic Dibasic Acids, *Makromol. Chem.* 56, 10 (1962).

Yoda, Naoya and Miyake, Akihisa, Synthesis of Polyanhydride. I. Mixed Anhydride of Aromatic and Aliphatic Dibasic Acids, *Makromol. Chem.* 32 (10), 1120 (1959).

Hill, Julian W. and Carothers, Wallace H., Studies of Polymerization and Ring Formation. XIX Many-Membered Cyclic Anhydrides, *J. Amer. Chem. Soc.* 55, 5023 (1933).

Conix, A., Poly[1,3-bis(p-carboxyphenoxy)-propane anhydride], *Macromolecular Synthesis*, vol. 2, 95 (1966).

Hill, Julian W. and Carothers, Wallace H., Studies of Polymerization and Ring Formation. XIV. A Linear Superpolyanhydride and a Cyclic Dimeric Anhydride From Sebacic Acid, *J. Amer. Chem. Soc.* 54, 1569 (1932).

Leong, K. W., Brott, B. C. and Langer, R., "Bioerodible Polyanhydrides as Drug-Carrier Matrices, I: Characterization, Degradation and Release Characteristics", *Journal of Biomedical Materials Research* 19, 941 (1985).

Leong, K. W., D'Amore, P., Marletta, M. and Langer, R., "Bioerodible Polyanhydrides as Drug-Carrier Matrices, II. Biocompatibility and Chemical Reactivity", *Journal of Biomedical Materials Research* 20, 51 (1986).

Rosen, Chang, Wnek, Lindhardt, and Langer, "Bioerodible Polyanhydrides for Controlled Drug Delivery", Biomaterials 4, 131-133 (1983).

Yoda, N., Synthesis of Polyanhydrides III., *Makromol. Chem.* 55 174-190 (1962).

Leong, et al., "Synthesis of Polyanhydrides: Melt-Polycondensation, Dehydrochlorination, and Dehydrative Coupling", *Macromolecules*, vol. 20, no. 4, 705-712 (Apr., 1987).

BIOERODIBLE ARTICLES USEFUL AS IMPLANTS AND PROSTHESES HAVING PREDICTABLE DEGRADATION RATES

This is a continuation-in-part of U.S. Ser. No. 613,001 filed May 21, 1984 by Robert S. Langer, Howard Rosen, Robert J. Linhardt, and Kam Leong entitled "Bioerodible Polyanhydrides for Controlled Drug Delivery", which is a continuation of U.S. Ser. No. 477,710 filed Mar. 22, 1983, now abandoned.

FIELD OF THE INVENTION

The present invention is concerned with biocompatible articles suitable for surgical introduction in-vivo and is particularly directed to bioerodible articles which degrade predictably as biocompatible and non-toxic products.

BACKGROUND OF THE INVENTION

Synthetic polymeric compositions which are bioerodible and biocompatible have become increasingly important and valuable in recent years. One application for such compositions is as surgically implantable biomaterials or prosthetic articles for human and animal subjects in-vivo. Consequently, such biomaterials are articles which serve as implants, a tangible item to be inserted into a living site as for growth or formation of an organic union, or prostheses, artificial devices introduced into living tissues to replace a missing part of the body; these are exemplified by articles such as vascular grafts, biodegradable sutures and pellets, and orthopedic appliances such as bone plates and the like. In order for an implantable or prosthetic article to be truly useful, it should be composed of a synthetic polymeric composition having specific characteristics and properties: First, the polymeric composition should have a surface that permits and encourages growth of appropriate mammalian cell types; that is, the growing and maintenance of cells on, and if appropriate, within, its matrix, after introduction into a subject in-vivo. For the purposes of graft materials, one objective is to maintain non-thrombogenic surfaces similar to that as exists in living tissues. A failure to initiate and maintain such endothelial cell surface layers leads to the occurrence of thrombotic events such as occlusion of the blood vessel(s) an ultimate failure of the implanted or prosthetic article. Second, the synthetic composition should provide sufficient elasticity and tensile strength over a preselected minimal time period which will vary with the specific application. Third, the synthetic composition should be non-immunogenic, biocompatible, biodegradable in-vivo and yield degradation products which are themselves non-inflammatory, non-toxic, and non-antigenic. Lastly, the ideal material should degrade within predictable periods of time and be suitable for introduction at multiple tissue sites thereby eliminating the need for surgical removal.

Despite continuing research efforts, no class of synthetic polymeric biomaterials has yet been developed which provides all these desired attributes. For example, most of the research concerning synthetic grafting materials has utilized compositions such as Dacron [Graham et al., *Arch. Surg.* 115:929–933 (1980); Herring et al., *Ann. Surg.* 190:84–90 (1979)]. These materials, however, never develop the desired endothelial cell intima necessary to maintain a non-thrombogenic surface; as a result, thrombosis—blood vessel blockage and diminished blood cell supply to organs in the body—often occurs. Similarly, the use of polygalactin mesh has failed to provide the necessary surface erosion characteristics and thus is unpredictable in degradation time [Bowald et al., *Surgery* 86:722–729 (1979)]. Other presently known biodegradable polymers such as polylactic acid, polyglycolic acid, polycaproloctones and the various polyamides also all degrade irregularly and unpredictably with a demonstratable loss of permeability and mechanical strength over time [Heller et al., "Theory and Practice of Control Drug Delivery from Bioerodible Polymers", in *Controlled Release Of Bioactive Material,* R. W. Baker Editors, Academic Press, New York, 1980, pp. 1–17; Pitt et al., *Biomaterials* 2:215–220 (1981); Chu, C. C., *J. Appl. Polym. Sci.* 26:1727–1734 (1981)]. Insofar as is presently known, therefore, no synthetic polymeric composition offers all the properties and characteristics which would make it desirable for use as an article for prosthesis or implantation in-vivo.

SUMMARY OF THE INVENTION

A bioerodible article useful for prosthesis and implantation and methods for its manufacture are provided which comprises a biocompatible, hydrophobic polyanhydride matrix, prepared in preselected dimensions and configurations, which erodes predictably into non-toxic residues after introduction in-vivo. The method of using the article as an implant and prosthesis comprises the step of introducing a specifically configured article into a subject in-vivo at a predetermined site.

DETAILED DESCRIPTION OF THE DRAWING

The present invention may be more completely and easily understood when taken in conjunction with the accompanying drawing, in which.

DETAILED DESCRIPTION OF THE PREFERRED EMBODIMENTS

Figure 1:
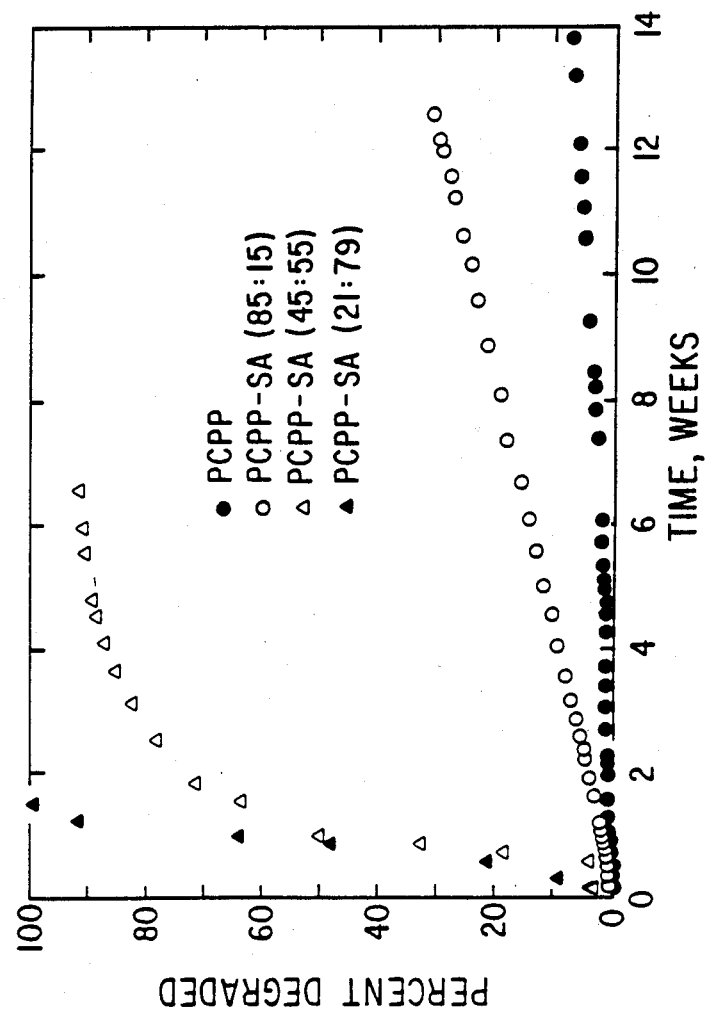
FIG. 1 is a graph illustrating the degradation rates for poly [bis (p-carboxyphenoxy) propane anhydride] matrices and its sebacic acid copolymer matrices at 37° C.

The present invention comprises articles useful as implants or prostheses and methods for their preparation and use. These articles comprise a biocompatible, bioerodible, hydrophobic class of synthetic polyanhydride polymeric compositions having the general formula:

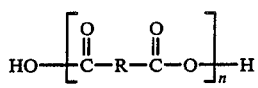

wherein, R is a hydrophobic organic group and n is greater than 1. This class of polymeric compositions can be formed in preselected dimensions and specific configurations. Regardless of the specific application, these compositions degrade within predictable periods of time after introduction in-vivo into non-toxic, non-inflammatory, and non-immunogenic residues.

The preferred embodiments of the R group within the general formulation given above is exemplified by, but is not limited or restricted to, the entities given in Table I below.

TABLE I

R Group (a) $-(CH_2)_x-$ wherein $x \geq 2$ and $\leq 16$ (b) a cyclohexyl group (c) a phenyl group with $-C(O)-O-C(O)-(CH_2)_x-$ wherein $16 \geq x \geq 2$ (d) two phenyl groups linked by $-O-(CH_2)_x-O-$ wherein $x \geq 1$ (e) $-(CH_2CH_2)_x-$phenyl$-(CH_2CH_2)_y-$ wherein $x \geq 1$ and $y \geq 1$, (f) substituted phenyl groups with R' and R'' substituents, wherein R' and R'' are organic groups The entire class of polyanhydrides can be synthesized using alternative methods of polymerization now known in the art: bulk polymerization [Conix, A., *Macro Synth.* 2:9598 (1966)]; solution polymerization [Yoda et al., *Bull. Chem. Soc. Japan* 32:1120–1129 (1959)]; and interfacial polymerization [Matsuda et al., Japanese Patent No. 10,944 (1962)]. Using any of these methods, a variety of different synthetic polymers having a broad range of mechanical, chemical, and erosion properties are obtained; the differences in properties and characteristics are controlled by varying the parameters of reaction temperatures, reactant concentration, types of solvent, and reaction time. This is true for all potential embodiments of R within the general formula stated above as well as the entities listed in T1 and the specific embodiments described in the Examples which follow herein.

All of the articles useful as prostheses or implants are synthetic polyanhydride polymeric compositions which share a number of demonstrable qualities in common:

1. Each of the articles displays predictable degradation rates when introduced in-vivo in a subject. Regardless of the exact composition, size and configuration, these articles erode only at their exterior surfaces without affecting the center of the matrix in any way. As the surfaces continue to progressively erode, the articles become thinner and smaller and eventually vanish completely from the tissue.

Predictable times for degradation is a consequence of biomaterials which erode by surface (or heterogeneous) erosion rather than by bulk (or homogeneous) erosion. Surface erosion is degradation which occurs only at the exterior surfaces of the composition which, in turn, become progressively thinner with the passage of time. Accordingly, by careful selection of the specific composition and control of the physical dimensions of the article, the user can preselect predictable times for complete degradation to occur.

2. The rate(s) of degradation for all entities within the class of polyanhydride polymeric compositions as a whole is not only predictable, but may also be controlled by varying the hydrophobicity of the polymer. The mechanism of predictable degradation requires that the polyanhydride polymers be hydrophobic in nature thereby preventing water from entering into the interior of the matrix in any appreciable degree. This may be achieved alternatively either by substituting one monomer (the R group) in the general formula for another or by combining two monomeric units as a copolymer and then utilizing the copolymer as the functional R group within the composition. This is exemplified by the use and attributes of the monomer poly (carboxyphenoxy) propane alone and in combination with sebacic acid as a copolymer. Although each of these compositions contains individual hydrophobic properties, each of these polyanhydride polymeric compositions contains water-labile linkages between its monomer (or copolymer) R units which after introduction into the subject either react with or become hydrolyzed by the subject's tissues and body fluids.

3. The rates of degradation for each individual polymeric composition within the general class of polyanhydride polymers are predictable and constant at a single pH level and present different and distinctive rates of degradation with small changes of pH. This permits the articles to be introduced into the subject at a variety of tissue sites; this is especially valuable in that a wide variety of articles and devices to meet different but specific applications may be composed and configured to meet specific demands, dimensions, and shapes—each of which offers individual, but different, predictable periods for degradation.

4. The entire class of polyanhydride polymers are biocompatible and bioerodible. In view of their intended function as an implant or prosthesis to be introduced into a subject in-vivo, it is absolutely required that these compositions be non-inflammatory, non-toxic, and non-immunogenic; that is biocompatible with the subject's tissues and body fluids in all respects 5. Implantable articles and prostheses formed of polyanhydride polymers do not measurably affect or influence living cells or tissues in any degree. Various polyanhydride compositions may be combined with large vessel endothelial cells and/or smooth muscle cells without inhibiting or affecting cell growth. In-vitro studies show that the endothelial or muscle cells maintained a non-overlapping, contact-inhibited monolayer of living cells throughout the testing period of two weeks. Subsequently made histological studies of these cultured specimens revealed attenuated endothelial monolayers over the exterior surfaces of the polymeric matrices which strongly resemble intimal endothelial monolayers in-vivo.

6. The articles comprising the present invention degrade (erode) into residues or moieties which are themselves biocompatible and non-toxic. As evidenced by the Examples which follow, each of the articles, regardless of specific polyanhydride formulation used, may be implanted into the cornea of rabbits without causing inflammation even in a minor degree; this is in stark contrast to presently known compositions (such as polylactic acid matrices) which demonstrate at least minor inflammation of such corneal tissues. Moreover, articles comprising polyanhydride compositions are demonstratably biocompatible as will be described in a study involving subcutaneous implantation of such articles in rats. Despite their presence in the living tissues over a period of weeks, no inflammatory cell infiltration (polymorphonuclear leukocytes, macrophages, and lymphocytes) is seen in the tissues adjacent to the implant. Equally important, as the article predictably degrades, the degradation products are demonstrably non-mutagenic, non-cytotoxic, and non-teratogenic.

It will be appreciated that these properties and characteristics, as well as the mechanical and chemical attributes, identify and distinguish such articles as being singularly suitable as implants or prostheses. The Examples which follow merely serve to illustrate one or more of the above described characteristics, which are representative of the entire class as a whole.

EXAMPLE 1

The articles prepared and tested were forms of poly [bis (p-carboxyphenoxy) propane anhydride] (hereinafter "PCPP") and its copolymers with sebacic acid (hereinafter "PPCP - SA"). These poly [bis (p-carboxyphenoxy) alkane anhydrides] were synthesized by melt polycondensation following the method of Conix [*Macro Synthe.* 2:95-98 (1966)]. Briefly summarized, the dicarboxylic acid monomers (or copolymers) were converted to the mixed anhydride by total reflux in acetic and anhydride. Caution was taken to avoid excessive reaction, which would yield a highly insoluble prepolymer difficult to purify; 30 minutes was deemed sufficient. The prepolymers isolated were further recrystallized in a 50:50 (v/v) mixed solvent of acetic anhydride and dimethylformamide. A recrystallization period of several weeks was sometimes necessary to obtain a reasonable yield (30%). The prepolymers then underwent melt polycondensation in vacuo under nitrogen sweep. The prepolymers were prepared by reacting different monomer ratios with acetic anhydride. Attempts were also made to obtain the copolymers by polycondensing the mixture of individually prepared prepolymers. In terms of controlling the final composition and purity of the product, the latter approach was found to be superior; however, because of the difficulty of isolating the sebacic acid anhydride prepolymer, the former method was deemed more convenient. Regardless of the methodology used, the composition of the copolymers were determined by ultraviolet spectrometry and weight analysis after decomposition in 1M NaOH at 70° C. overnight.

The resulting polymers were purified by extraction with anhydrous ether in a Soxhlet E extractor for several hours and then stored in a dessicator over calcium chloride. The purified polymers, obtained as a crystalline solid, were then ground in a Micro Mill Grinder and sieved into a particle size ranging from 90-150 micrometers (hereinafter "μm"). The polymer particles were then pressed into circular disks using a Carver Test Cylinder Outfit at 30 KPSI at 5° C. above the polymer's glass transition temperature, TG, for ten minutes. Those polymeric compositions that had glass transition temperatures below 30° C. were molded at room temperature. The dimensions of the circular disks were 14 millimeters (hereinafter "mm") in diameter, 0.9-1.1 mm thick, and weighed between 140 and 160 milligrams (hereinafter "mg").

The degradation characteristics of such synthetic polyanhydrides are demonstrated by hydrophobic disks comprising PCPP; PCPP and PCPP-SA in 85:15 ratio; PCPP-SA in a 85:15 ratio; PCPP-SA in a 45:55 ratio; and PCPP-SA in a 21:79 ratio. Circular disks comprising each of these compositions were placed in 0.1M phosphate buffer, pH 7.4 at 37° C. for a time period of up to 14 weeks. The results are given in FIG. 1 as degradation profiles whose erosion kinetics were followed by measuring the ultraviolet absorbance at 250 nanometers (hereinafter "nm") of periodically changed buffer solutions using a Perkin-Elmer UV Spectrophotometer model 553. As is readily seen, the more hydrophobic polymers—PCPP and PCPP-SA (85:15)—displayed constant erosion kinetics over several months. Moreover, as the sebacic acid content increased in the polymeric composition, the polymers became more hydrophilic and demonstrated increased rates of erosion. The rate of erosion for the composition in fact increased 800 times when the sebacic acid content of the polymer reached 80 percent. It was also noted that the more hydrophilic copolymer compositions, PCPP-SA (45:55) and (21:79) tended to crumble in the later stages of degradation.

A separate study investigated the affect of increasing the size of the alkane monomer and its affect on degradation rate in the homologous poly [bis (p-carboxyphenoxy) alkane] series. It was found that as the number of methylene units in the R group backbone was increased, the polymeric composition became more hydrophobic and the degradation rates decreased several orders of magnitude. Specifically, as the methylene units were increased from 1 to 6 in the composition, the degradation rate underwent a decrease of 3 orders of magnitude. By extrapolation of the data in FIG. 1, the PCPP polymer is predicted to degrade completely and slightly over 3 years' time; it is also therefore apparent that the predictable time for degradation can be increased or decreased at will by several orders of magnitude by either increasing or decreasing the alkane size.

EXAMPLE 2

Figure 2:
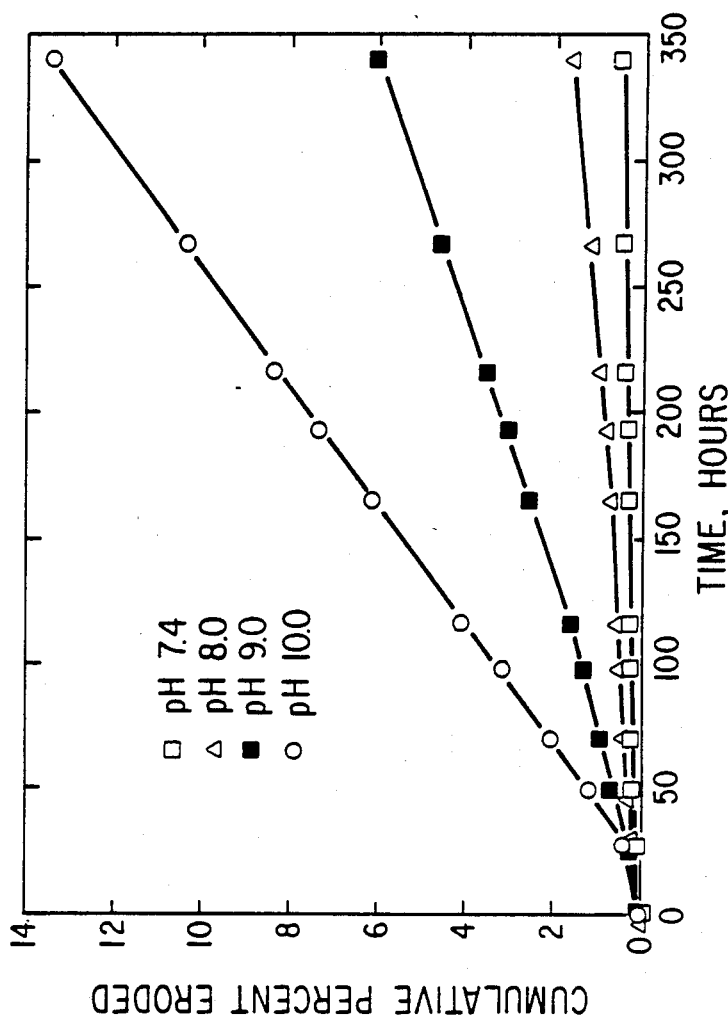
FIG. 2 is a graph illustrating the degradation rates for compression molded poly [bis (p-carboxyphenoxy) propane anhydride] at different pH levels ranging from 7.4 to 10.0.

The degradation rates for PCPP at a variety of pH levels ranging from 7.4–10.0 were determined. The PCPP was prepared, purified, and compression molded into circular disks as described earlier in Example 1. Each disk was placed in 10-50 milliliters (hereinafter "ml") of phosphate buffer held at 37° C. which was prepared at specific pH levels. The erosion of the disk was again followed by UV absorbance at 250 nm over a test period of 350 hours. The results are illustrated in FIG. 2 which demonstrates that the rate of degradation is increased by a factor of 20 as the pH is increased from 7.4 to 10.0. It is also noteworthy that the rates of degradation remain stable and constant during the entire two week testing period.

EXAMPLE 3

The biocompatibility and toxological effects were investigated using the representative polyanhydride polymers PCPP, PCPP-SA (45:55) poly (terephthalic acid anhydride) hereinafter "PTA", and poly (terephthalic-sebacic acid anhydride) hereinafter "PTA-SA" in a 50:50 ratio. The polymers PCPP and PCPP-SA (45:55) were prepared in the manner described in Example 1. PTA and PTA-SA (50:50) were synthesized in solution by an adaptation of the method of Yoda and Matsuda [Bull. Chem. Soc. Japan 32:1120–1129 (1959); Japanese Patent No. 10944]. This technique of solution polymerization utilizes a dehydrative coupling reaction between an acyl chloride and a carboxyl group to obtain the polymer. This polymerization technique is preferrable because the high melting point (372° C.) of the PTA polymer and its instability (charring) at this temperature made the melt-polycondensation methodology unsuitable. Preferrably, 0.02 mole of terephthalic acid (or 0.02 mole of sebacic acid) was dissolved in 400 ml of chloroform in the presence of 0.04 mole of triethylamine. Terephthaloyl chloride (0.02 mole) previously dissolved in benzene was added through a dropping funnel over a 30 minute period under vigorous agitation. This mixture was allowed to react for three hours at room temperature and was held under a nitrogen sweep at all times. The resulting polymer, PTA or PTA-SA (50:50) was then purified by extraction with anhydrous ether in a Soxhlet Extractor for 2–3 hours and was then stored in a dessicator over calcium chloride.

All samples for toxicological studies were prepared by placing each polymer in 0.1M phosphate buffer, pH 7.4, for several days and allowing the polymer to degrade. The concentration of the degradation products was then determined by ultraviolet spectrophotometry. The cytotoxicity and mutagenicity of the respective degradation products for the copolymer PCPP-SA (45:55) were determined by a forward mutation assay in *Salmonella typhimurium* using 8-azaguanine resistance as a genetic marker as described in Skopec et al., *Proc. Natl. Aca. Sci. U.S.A.* 75:410–414 (1978). This mutagenicity assay also includes a test for toxicity so that the mutagenicity, if present, can be expressed quantitatively as the number of mutants per surviving cell. In this way, an independent measurement of toxicity for this bacterial species can be obtained. Samples of PTA-SA (50:50) were tested at 1 mg/ml both with and without the addition of mammalian metabolism enzymes. The results of this assay demonstrated that the degradation products of this polymer were non-mutagenic with or without the addition of a mammalian metabolizing system. In all instances, the induced mutant fraction was essentially 0 being indistinguishable from the spontaneous background control. Similarly, there was no toxicity in any sample without the addition of metabolic enzymes and a slight, but not significant, toxicity in samples with the metabolizing system.

The teratogenic potential was measured using a newly developed in-vitro assay in which the attached efficiency of ascetic mouse ovarian tumor cells to plastic surfaces coated with concanavalin A was determined [Braun et al., *Proc. Natl. Aca. Sci. U.S.A.* 79:2056–2060 (1982)]. In general with this assay, non-teratogens do not inhibit attachment of the tumor cells to the plastic surfaces. The degradation products of each respective polymer in phosphate buffer solutions was titrated to pH 7.4 with NaOH before the tests were conducted since the attachment is sensitive to acidic pH levels. The reaction mixture of degradation products and tumor cells was allowed to react for 2 hours at room temperature and a cell suspension was buffered with 50 mM of HEPES buffer during the two hour incubation period. The preferred concentration for each sample was 0.035 mg/ml. The teratogenicity test results indicated an average decline in attachment efficiency of 35 ±3%. Given that the criteria for potential teratogenicity is an inhibition of cell attachment by more than 50%, the degradation products of these polyanhydride compositions are considered non-teratogenic.

Figure 3A:
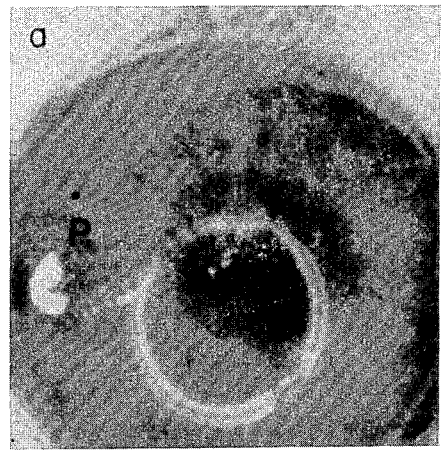
FIGS. 3a and 3b is a set of two photographs illustrating the biocompatibility attributes of the present invention in-vivo as corneal implants in rabbits one week after introduction.
Figure 3B:
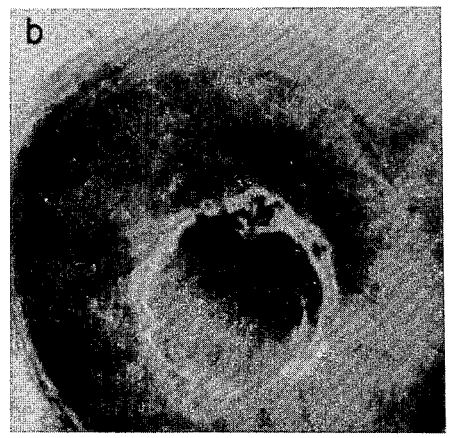
Figure 4:
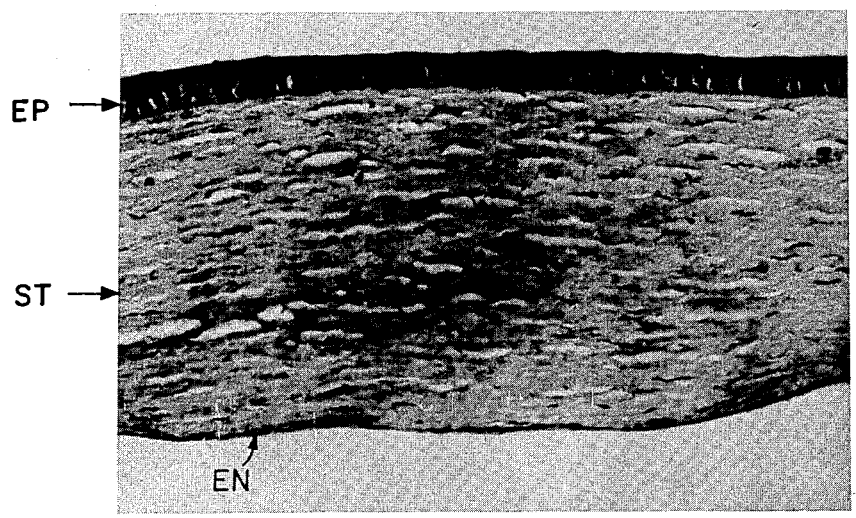
FIG. 4 is a photograph illustrating a magnified view of the rabbit cornea of FIG. 3 in cross section.

Testing in-vivo for the localized tissue response to the polymers was determined by implantation in the corneas of rabbits and subcutaneous introduction in rats. For this series of tests, PCPP and PTA-SA (50:50) were fashioned into pellets whose dimensions were 1 mm×1 mm×0.5 mm and implanted surgically in rabbit intracorneal pouches within the corneal stroma following the methodology described in Langer et al., *J. Biomed. Mat. Res.* 15:267–277 (1981). The rabbit corneas were then inspected twice weekly by stereomicroscopy for signs of inflammation as manifested by edema, cellular infiltration, and neovascularization for a period of six weeks. The host response to the polymeric pellets implanted in the rabbit corneas is seen in FIGS. 3a and 3b. FIG. 3a is the stereomicroscopic observation of the cornea one week after implantation; FIG. 3b shows the same cornea after the polymeric pellet had completely degraded after six weeks. No inflammatory response or characteristics were observed at any time over the entire six week implantation and degradation period; furthermore, the clarity of the corneas was maintained and the proliferation of new blood vessels absent in all instances. In addition, after the six week testing period, each cornea was surgically removed and prepared for histological examination to confirm and verify the accuracy of the stereomicroscopic data. A representative cross section of rabbit cornea is seen in FIG. 4 which provides a highly magnified view of the epithelial cell layer EP, the cornneal stroma ST, and the endothelial cell layer EN. As is apparent there is a total absence of inflammatory cells throughout the corneas and this tissue appears normal in all respects.

Figures 5A, 5B:
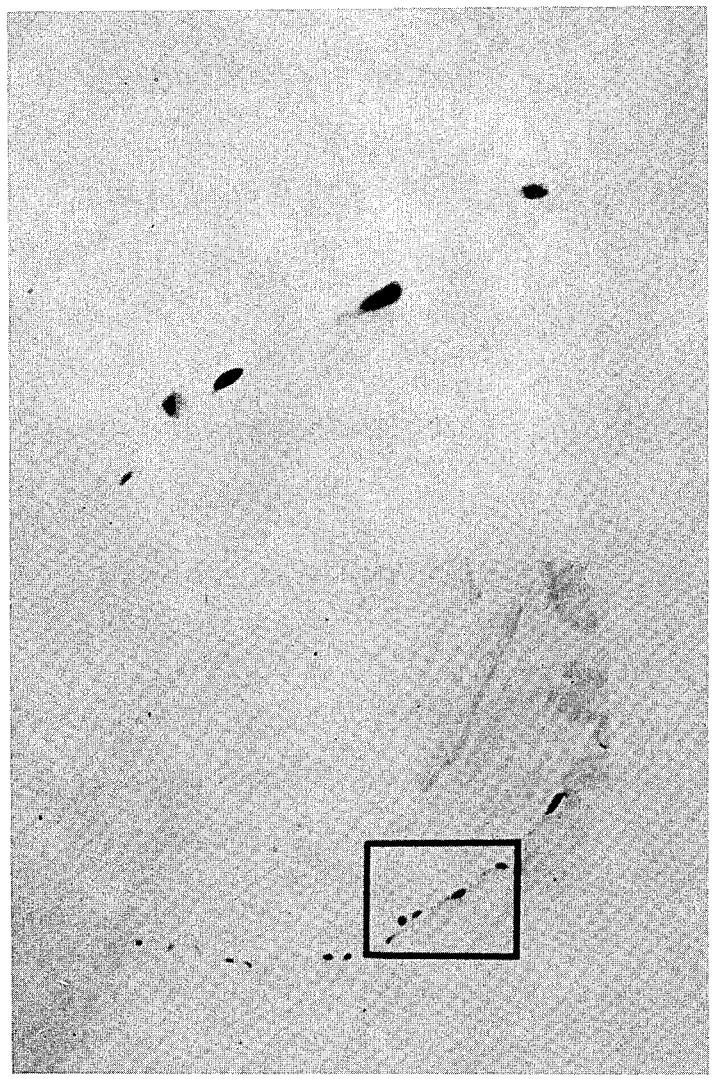
FIGS. 5a and 5b is a set of two photographs visualizing a magnified view of rat skin tissue in cross section following a six month period of subcutaneous implantation of the present invention.

The in-vivo tissue response was determined by subcutaneously implanting PCPP pellets in the abdominal region of Sprague-Dawley rats following the procedure of Brown et al., *J. Pharm. Sci.* 72:1181–1185 (1983). After surgical introduction of the polymer pellet into the rat, the animals were maintained normally for a six month period without special attention. The rats were then sacrificed and histological sections of the abdominal tissues surrounding the site of implantation prepared and studied. The results are illustrated in FIG. 5a and 5b. FIG. 5a is a magnified cross-sectional view of the abdominal muscle wall in cross section showing skeletal muscle and blood vessels; FIG. 5b is the identical tissue seen at a greater degree of magnification. It is apparent in each instance that no inflammatory cell infiltration, that is the appearance of polymorphonuclear leukocytes, macrophages and lymphocytes, is seen in the tissues adjacent to the implantation site. Similarly, gross post mortem inspection also did not reveal any abnormalities of any kind at the implantation site.

EXAMPLE 4

To demonstrate the biocompatibility and non-toxic properties of polyanhydride polymeric compositions as a whole, additional in-vitro tissue culture studies were performed using PCPP-SA (45:55), PTA-SA (50:50) and PTA, each of which was prepared as previously described. The tissue culture studies relied on the ability of endothelial cells and smooth muscle cells to grow and be maintained in culture on the surface of these polymers. Endothelial cells were isolated from bovine aortas by collagenase digestion and then cultured in-vitro using the procedures described in Jaffe et al., *J. Clin. Invest.* 52:2745–2756 (1973). The identity of these endothelial cells was confirmed by staining for the presence of Factor VIII antigen [Jaffe et al., *J. Clin. Invest.* 52:2757–2764 (1973). Smooth muscle cells were obtained by explantation of bovine aortic medial tissue following the methods of Ross, R., *J. Cell. Biol.* 50:172–186 (1971). At confluence, each cell type grew in a characteristic "hill and valley" morphology. Approximately $1.0 \times 10^4/cm^2$ cells which had been previously passed in culture 4–15 times were plated directly onto the circular pieces of polymer (having dimensions of approximately 1.5 $cm^2 \times 1$ mm) in a 0.25 ml drop of culture medium and allowed to react for one hour's duration at room temperature. The polymeric disks were then flooded with 15 ml of Dulbeccio's Modified Eagle's medium containing 10% calf serum in 100 mm containers. The culture medium was changed daily to avoid accumulation of the acidic polymer degradation products. After two weeks in culture at room temperature, the polymeric disks and adherent cells were rinsed with phosphate buffered saline, pH 7.2, and fixed for one hour with a 1% buffered glutaraldehyde solution.

Examination of the cultured cells and polymers reveal the following: the bovine aortic endothelial cells grew normally both over the surfaces of the polymers and in the Petri dish containing media and the degradation products of the polymer. In both instances the cells displayed a normal morphology of polygonal cells in a monolayer conformation typical of endothelial cells There was no evidence of any toxic effect on these cells whatsoever. Similarly, smooth muscle cells also grew normally over the surfaces of the polymers and in the presence of the degradation products. These smooth muscle cells were examined also for abnormalities on the basis of typical cell morphology or inhibition of their ability to proliferate. Deleterius effects were absent and growth was normal for all samples tested.

Figure 6A:
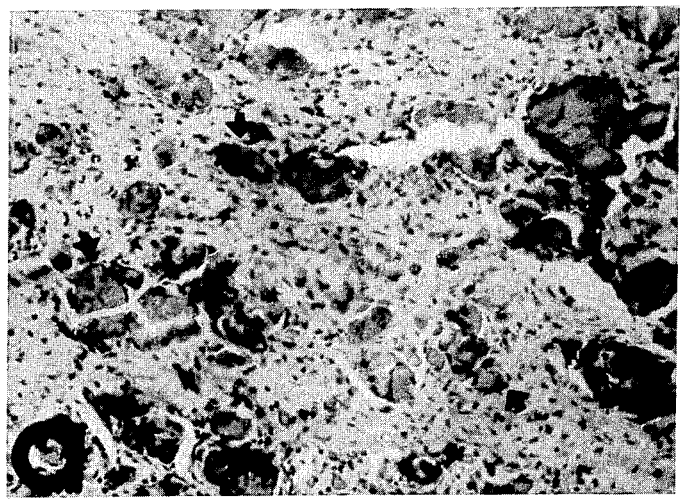
FIGS. 6a and 6b is a set of two photographs visualizing a magnified view of fixed polymer-cell complexes cultured in-vitro
Figure 6B:
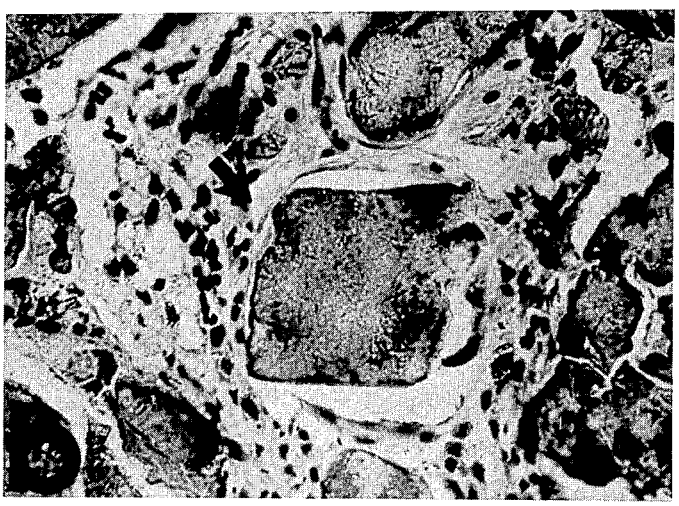

Moreover, it was found that both the endothelial cells and the smooth muscle cells grew and reproduced in approximately the same amount of time in the control samples utilizing polystyrene tissue culture plastic and using the polyanhydride polymeric substance. The doubling times for endothelial cells were 16±2.5 hours and 15±3.0 hours for the polystyrene plastic and the polyanhydride polymers respectively; similarly, the doubling growth times for smooth muscle cells was 8±1.5 hours and 8±2.0 hours using smooth muscle cells in the polystyrene plastic and polyanhydride polymers respectively. Gross visual observation of the attachment of both kinds of cells to the polyanhydride polymers was difficult if not impossible because of the opaque character of the polymers. For this reason, histological sections were prepared and stained to confirm the normal appearance and growth of each type of cell. Cross-sections of the fixed polyanhydride polymer-complexes are seen in FIGS. 6a and 6b which reveals the presence of growing endothelial cells as a flattened monolayer similar in character and appearance to endothelial cells growth as an intima layer on blood vessels in-vivo. There is no evidence of any enlarged cells, there are no vacuoles, and there is no loss of the normal growth pattern which would be visible if cell growth were compact-inhibited by the polyanhydride test samples or their degradation products.

Bioerodible and biocompatible polyanhydride polymeric compositions may be prepared in a wide variety of specific formulations and be formed into preselected dimensions and desired configurations as articles useful for implantation or prosthesis. Any of the presently known compression molding techniques, casting techniques, or other manufacturing processes may be used to fashion the article into the desired dimensions and configurations to meet the specific application. The variety and multiplicity of uses for such articles are exemplified by vascular graft materials, bioerodible sutures, artificial skin surfaces, and orthopedic devices generally such as bone plates and the like. In particular applications the articles may also contain additional substances such as collagen elastin, proteins and polypeptides which also aid and promote healing and repair of body tissues and organs.

After the articles have been formed into the desired dimensions and configurations, it is introduced into the subject in-vivo at a predetermined tissue site. It is expected that presently known surgical procedures will be used for introduction of the article as these are presently the most efficient and most reliable techniques. In certain instances it can be seen that alternate methods of introduction will also be useful. The specific site for introduction of the article is a matter of the user's need or choice and may be either subcutaneous, superficial, or deeply imbedded into the tissues or organs of the subject as the need arises. It will be recognized that the precise method of introduction and the particular site of implantation are of no consequence and are merely selected at will from the many procedures and applications suitable for use.

The present invention is not to be restricted in form nor limited in scope except by the claims appended hereto.

What we claim is:

1. An article useful for implantation or otherwise placed in or on the body, comprising a biocompatible, bioerodible, hydrophobic polyanhydride composition of the formula

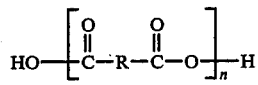

wherein R is an organic group and n is at least 2, said polyanhydride being purified and characterized by biocompatibility that results in minimal tissue irritation when implanted in vasculated tissue and degrading at predictable, constant rates by hydrolysis into non-toxic residues after introduction in vivo.

2. The article as recited in claim 1 wherein said R group is a hydrocarbon comprising from 2-16 carbon atoms.

3. The article as recited in claim 1 wherein said R group is

4. The article as recited in claim 1 where in the R group is

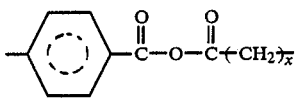

wherein x is not less than 2 and not more than 16.

5. The article as recited in claim 1 wherein said R group is

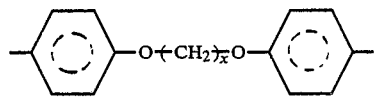

wherein x is at least 1.

6. The article as recited in claim 1 wherein said R group is

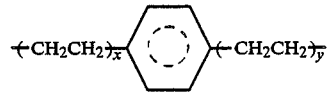

wherein x is at least 1 and y is at least 1.

7. The article as recited in claim 1 wherein said R group is selected from the group consisting of

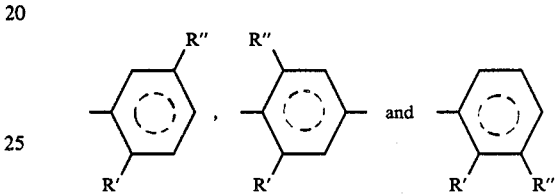

wherein R' and R" are organic groups.